US012453831B1

(12) United States Patent
Clark

(10) Patent No.: US 12,453,831 B1
(45) Date of Patent: Oct. 28, 2025

(54) HEATING APPARATUS FOR REMOVING MUCUS

(71) Applicant: Garland Clark, Rocky Mount, NC (US)

(72) Inventor: Garland Clark, Rocky Mount, NC (US)

( * ) Notice: Subject to any disclaimer, the term of this patent is extended or adjusted under 35 U.S.C. 154(b) by 807 days.

(21) Appl. No.: 17/839,583

(22) Filed: Jun. 14, 2022

(51) Int. Cl.
*A61M 16/06* (2006.01)
*A61M 16/16* (2006.01)

(52) U.S. Cl.
CPC ............ *A61M 16/06* (2013.01); *A61M 16/16* (2013.01); *A61M 2202/068* (2013.01)

(58) Field of Classification Search
CPC ................. A61B 18/02; A61B 18/025; A61M 1/682–684; A61M 2202/068
See application file for complete search history.

(56) References Cited

U.S. PATENT DOCUMENTS 2,028,889 A 1/1936 Baddour
2,410,903 A * 11/1946 Rogge .................. A61M 15/00 128/204.11
2,579,383 A 12/1951 Goudsmit
2,626,343 A 1/1953 Fogel
3,134,891 A 5/1964 Marina
3,152,240 A * 10/1964 Scott ...................... A61H 33/12 219/486
3,808,403 A 4/1974 Gunma
4,061,897 A * 12/1977 Thykeson ............... A61F 7/007 607/108
4,259,748 A * 4/1981 Miller .................... A45D 44/12 2/9
6,329,638 B1 12/2001 Bloodworth
6,910,931 B1 6/2005 Nakase
2008/0236612 A1* 10/2008 Duke-Obaigbena ... A45D 34/00 4/537
2017/0265533 A1* 9/2017 Gueritee ................ H05B 3/342

FOREIGN PATENT DOCUMENTS

CN 107184386 A * 9/2017 ............ A61H 33/12
CN 108324548 A * 7/2018 ........... A61H 33/065
CN 211835425 U * 11/2020
GB 2278544 A * 12/1994 ............ A61H 33/12
WO 1985001178 3/1985

* cited by examiner

*Primary Examiner* — Joseph D. Boecker
*Assistant Examiner* — Thomas W Greig
(74) *Attorney, Agent, or Firm* — Kyle A. Fletcher, Esq.

(57) ABSTRACT

The heating apparatus for removing mucus comprises a face mask and a chest cover. The face mask may be adapted to be worn adjacent to a face and may retain water between the face mask and the face. The chest cover may be adapted to be worn adjacent to a chest and may retain water between the chest cover and the chest. The face mask and the chest cover may heat when activated and may be adapted to evaporate water to create water vapor which may help to break up mucus located within the user's sinuses and throat. The temperature of the heat created by the face mask and the chest cover may be controlled via a first thermostat control and a second thermostat control, respectively.

16 Claims, 7 Drawing Sheets

HEATING APPARATUS FOR REMOVING MUCUS

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of mucus clearing devices, more specifically, a heating apparatus for removing mucus.

SUMMARY OF INVENTION

The heating apparatus for removing mucus comprises a face mask and a chest cover. The face mask may be adapted to be worn adjacent to a face and may retain water between the face mask and the face. The chest cover may be adapted to be worn adjacent to a chest and may retain water between the chest cover and the chest. The face mask and the chest cover may heat when activated and may be adapted to evaporate water to create water vapor which may help to break up mucus located within the user's sinuses and throat. The temperature of the heat created by the face mask and the chest cover may be controlled via a first thermostat control and a second thermostat control, respectively.

An object of the invention is to cover a face with a face mask comprising a first outer layer, a first inner later, and a first heating element where the first outer layer is waterproof and the first inner layer is absorbent.

Another object of the invention is to cover a chest with a chest cover comprising a second outer layer, a second inner later, and a second heating element where the second outer layer is waterproof and the second inner layer is absorbent.

A further object of the invention is to heat the face mask using the first heating element and to heat the chest cover using the second heating element such that water retained by the first inner layer and the second inner layer is converted into water vapor.

Yet another object of the invention is to control the operation and temperature of the face mask and the chest cover using a first thermostat and a second thermostat, respectively.

These together with additional objects, features and advantages of the heating apparatus for removing mucus will be readily apparent to those of ordinary skill in the art upon reading the following detailed description of the presently preferred, but nonetheless illustrative, embodiments when taken in conjunction with the accompanying drawings.

In this respect, before explaining the current embodiments of the heating apparatus for removing mucus in detail, it is to be understood that the heating apparatus for removing mucus is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the heating apparatus for removing mucus.

It is therefore important that the claims be regarded as including such equivalent construction insofar as they do not depart from the spirit and scope of the heating apparatus for removing mucus. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description. As used herein, the word "or" is intended to be inclusive.

Figure 1:
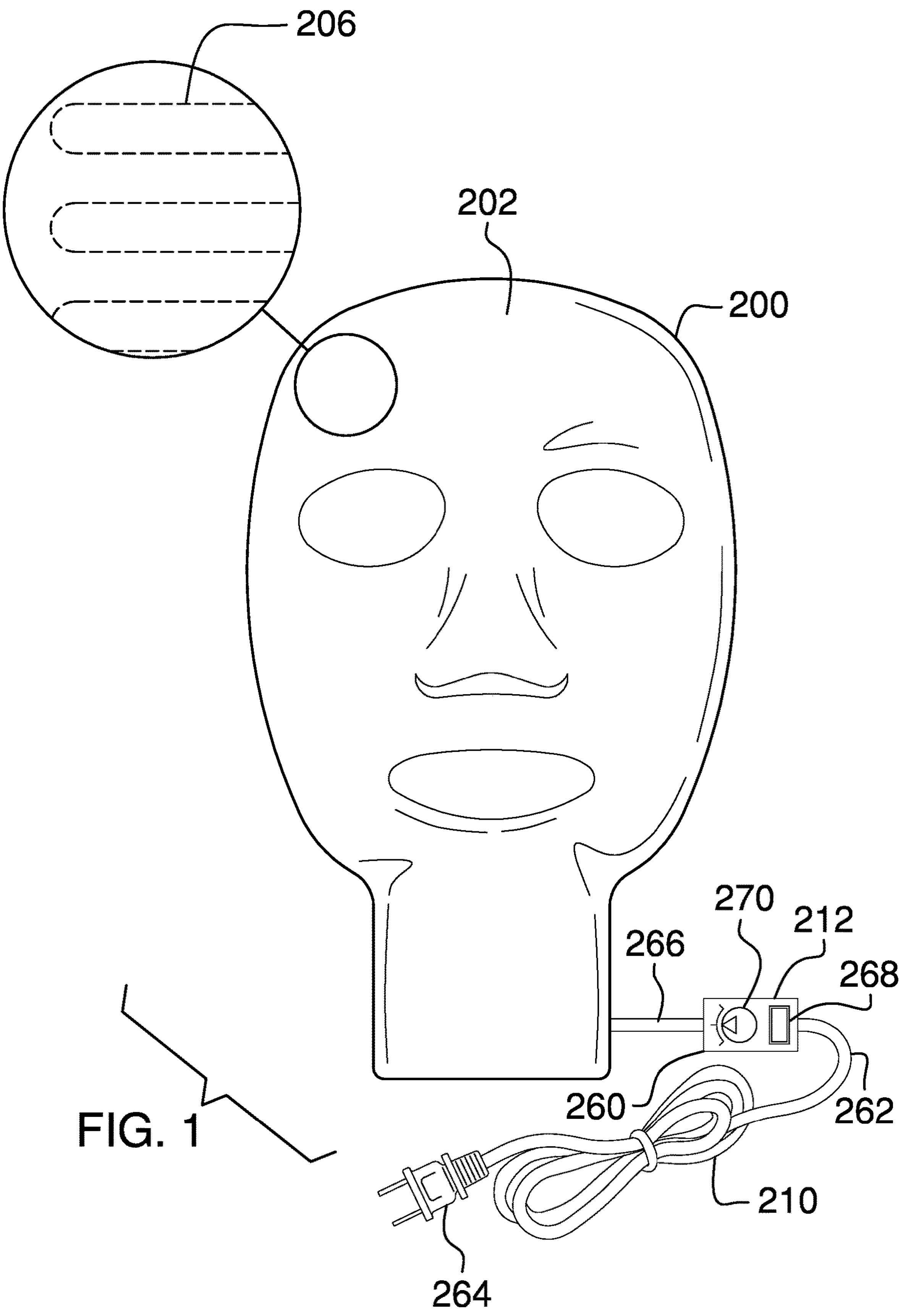
FIG. 1 is a front view of an embodiment of the disclosure illustrating the face mask.
Figure 2:
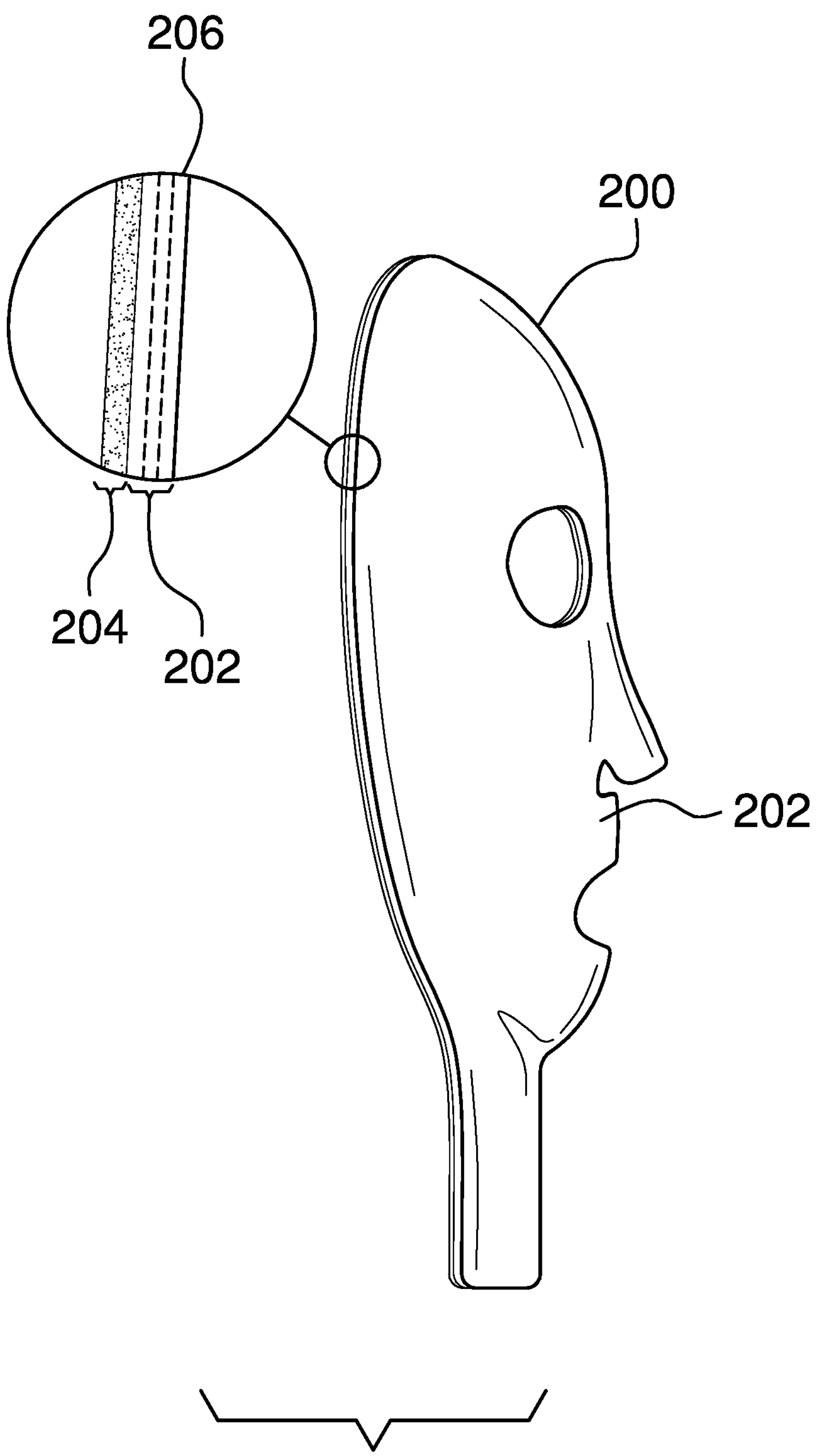
FIG. 2 is a side view of an embodiment of the disclosure illustrating the face mask.
Figure 3:
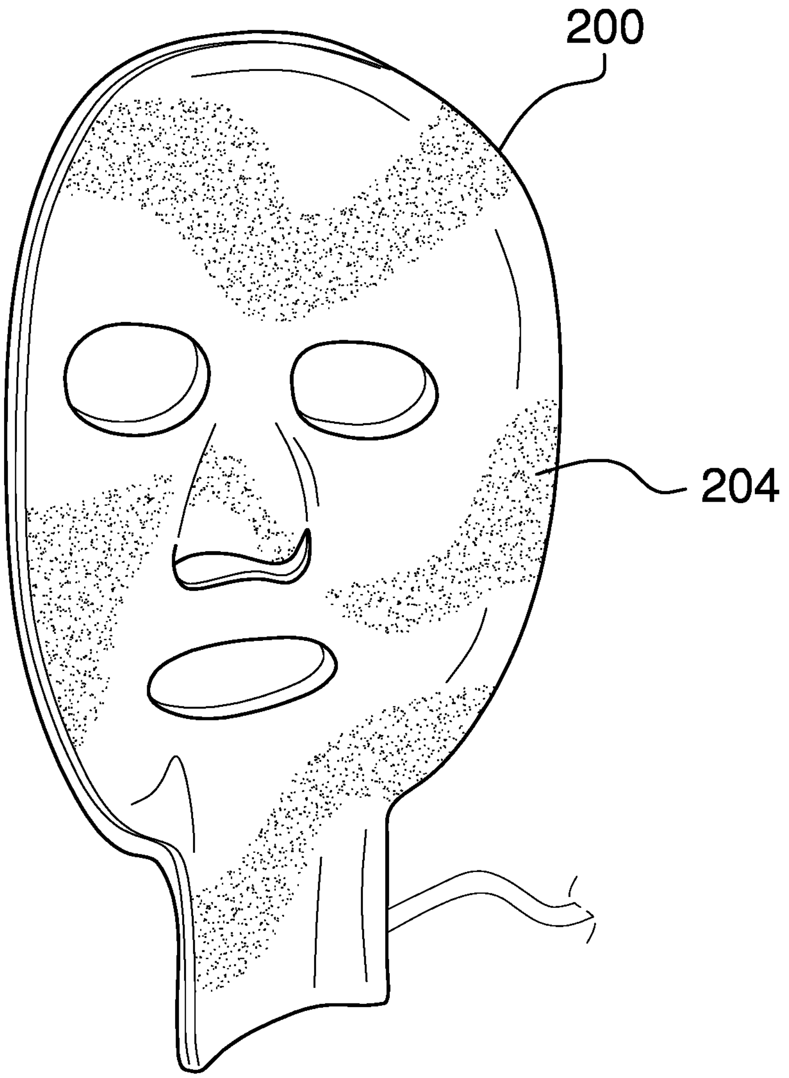
FIG. 3 is a rear isometric view of an embodiment of the disclosure illustrating the face mask.
Figure 4:
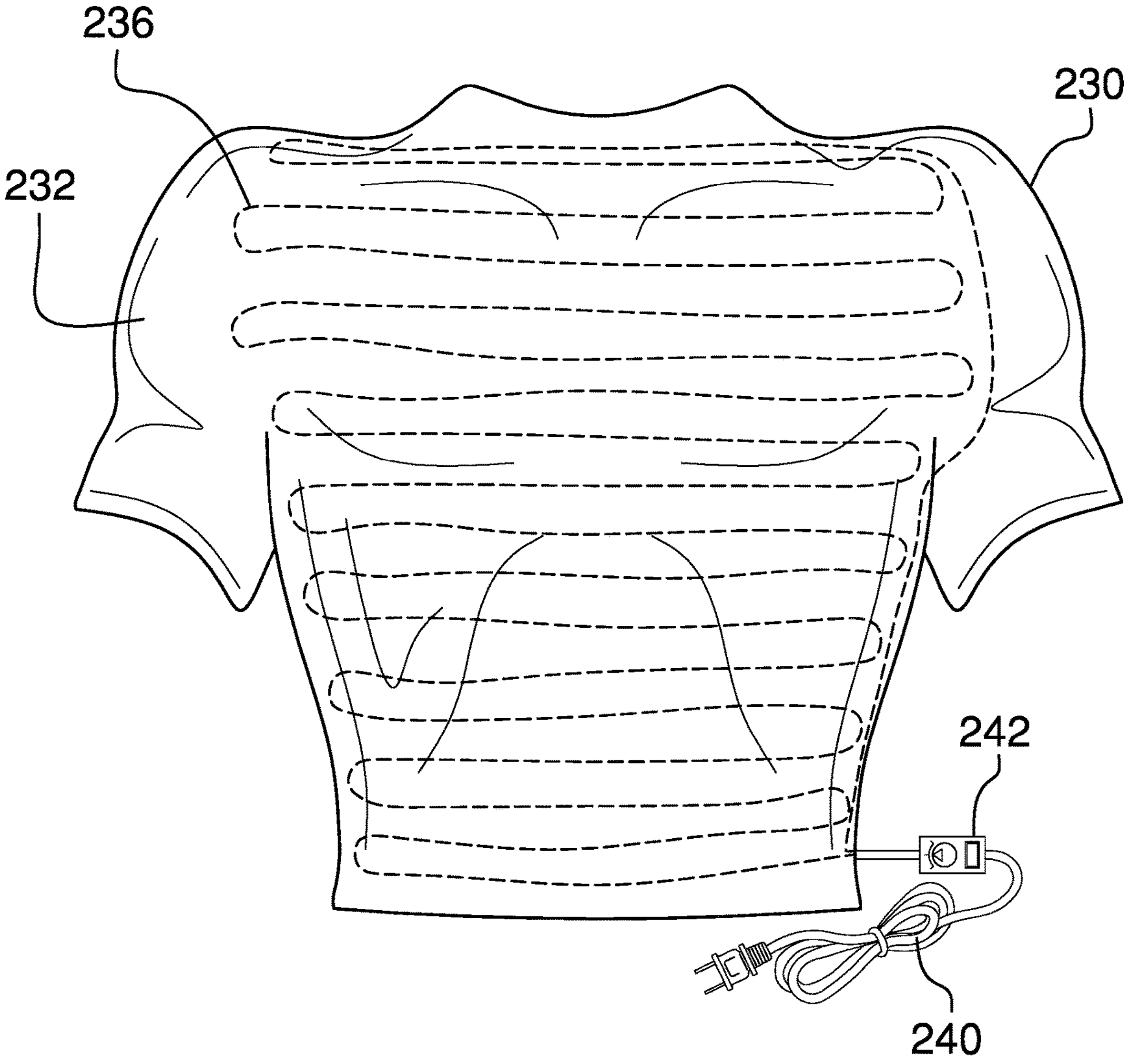
FIG. 4 is a front view of an embodiment of the disclosure illustrating the chest cover.
Figure 5:
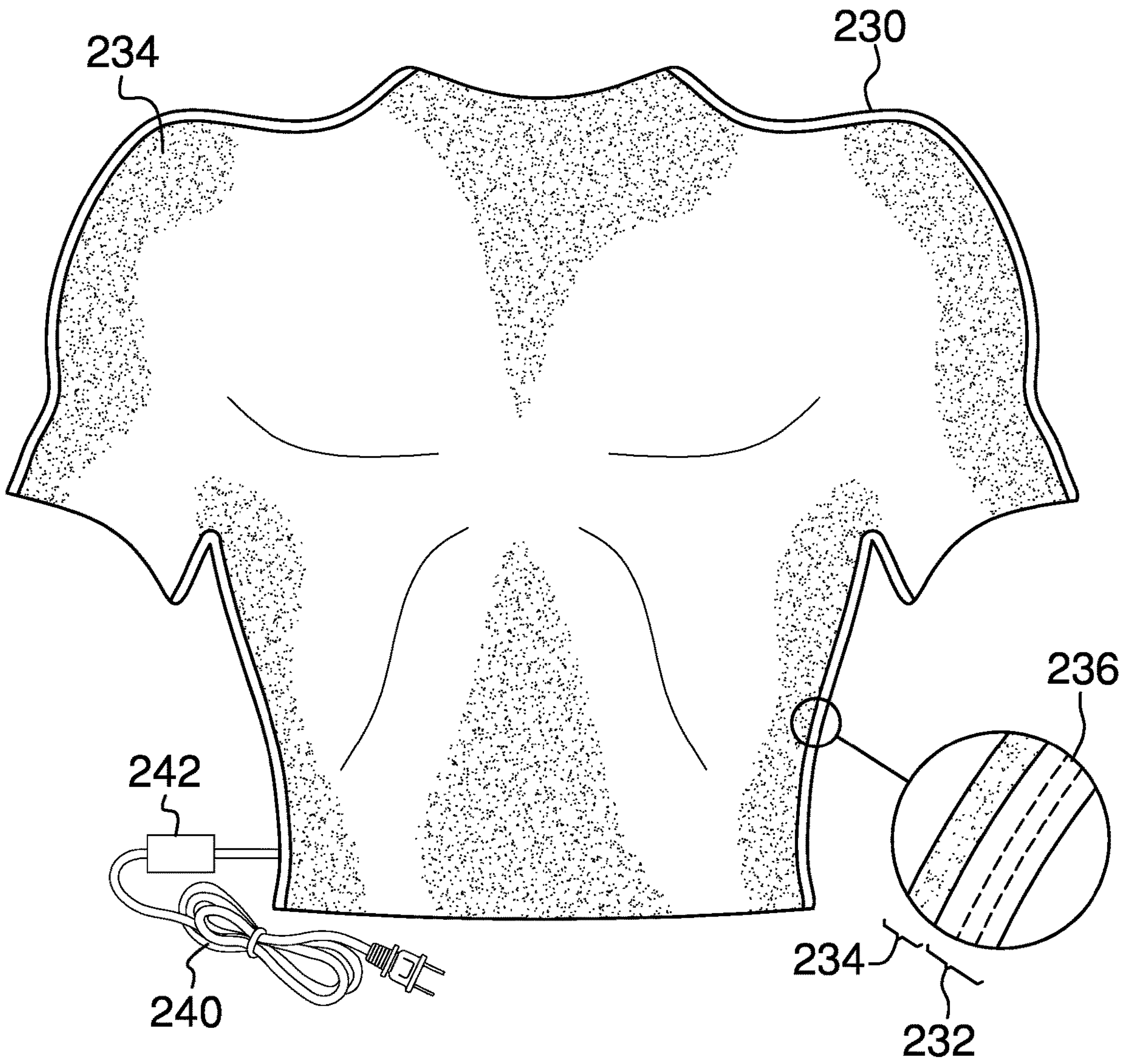
FIG. 5 is a rear view of an embodiment of the disclosure illustrating the chest cover.
Figure 6:
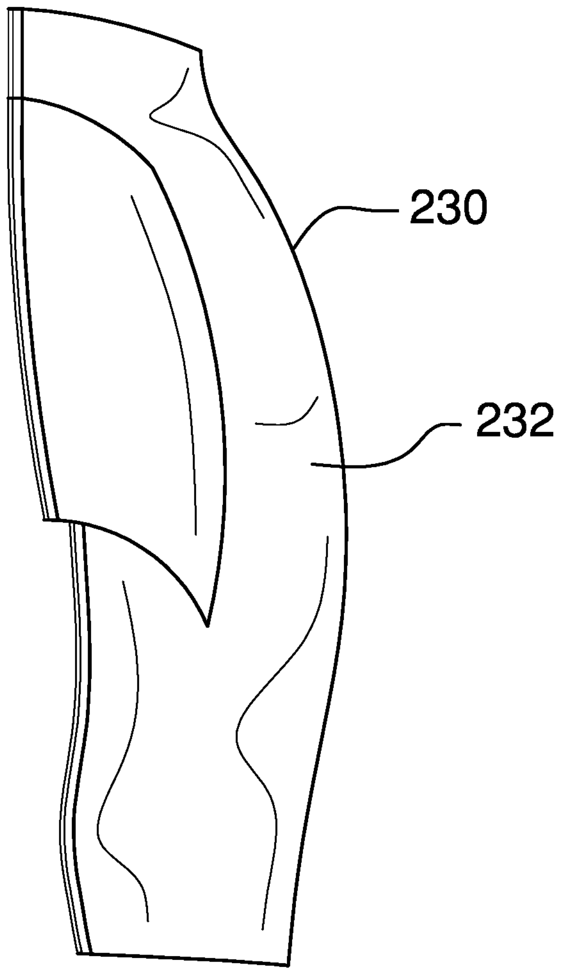
FIG. 6 is a side view of an embodiment of the disclosure illustrating the chest cover.
Figure 7:
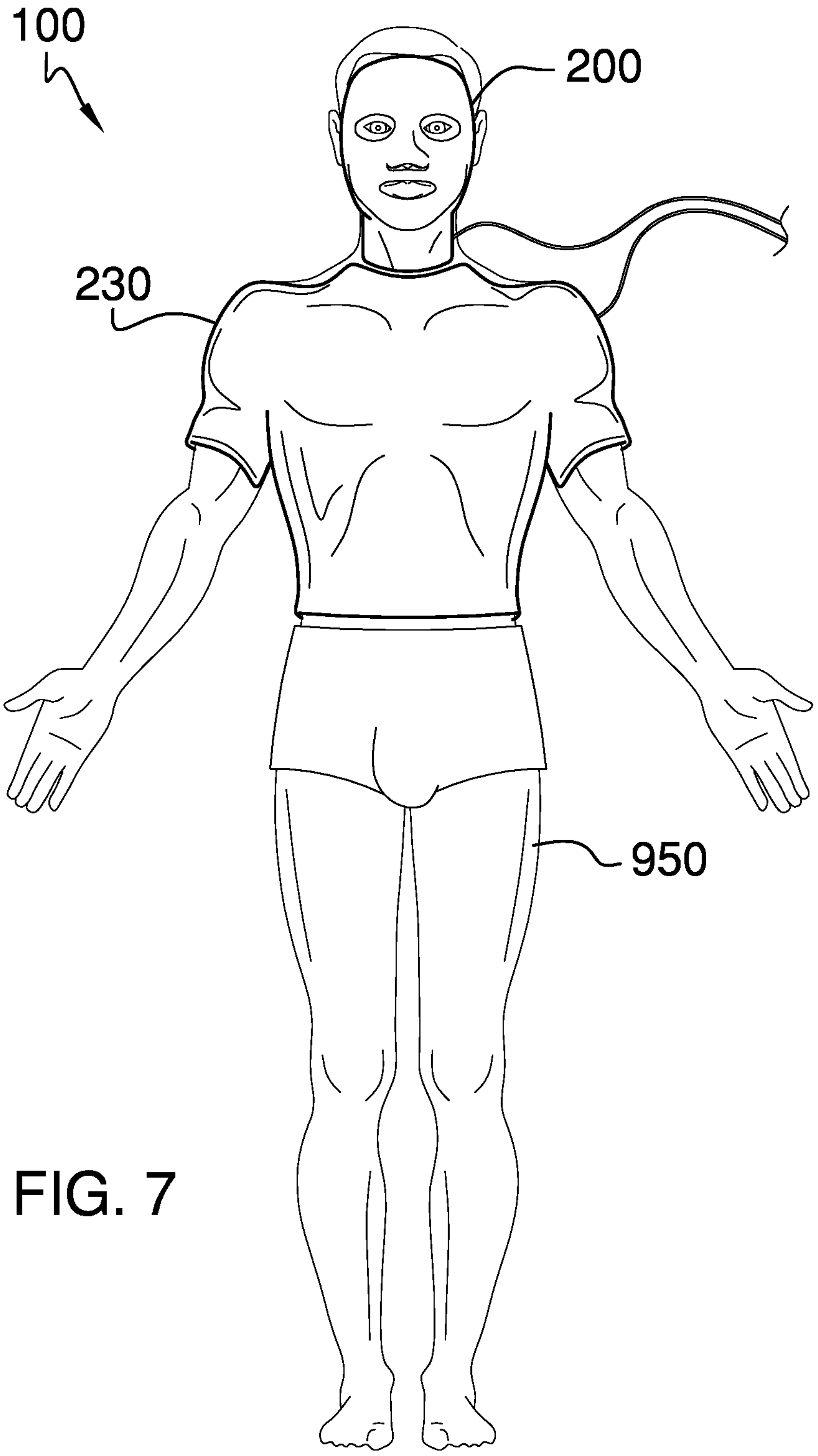
FIG. 7 is an in-use view of an embodiment of the disclosure.

Detailed reference will now be made to a first potential embodiment of the disclosure, which is illustrated in FIGS. 1 through 7.

The heating apparatus for removing mucus 100 (hereinafter invention) comprises a face mask 200 and a chest cover 230. The face mask 200 may be adapted to be worn adjacent to a face and may retain water between the face mask 200 and the face. The chest cover 230 may be adapted to be worn adjacent to a chest and may retain water between the chest cover 230 and the chest. The face mask 200 and the chest cover 230 may heat when activated and may be adapted to evaporate water to create water vapor which may help to break up mucus located within the user's sinuses and throat. The temperature of the heat created by the face mask 200 and the chest cover 230 may be controlled via a first thermostat control 212 and a second thermostat control 242, respectively.

The face mask 200 may be a shell that may be adapted to cover the face of a user 950. The face mask 200 may be adapted to follow the contours of the face such that a tight fit is assured. The face mask 200 may be adapted to provide apertures for eyes, mouth, and nostrils. The face mask 200 may be adapted to extends downwards to cover the front of a neck.

The face mask 200 may comprise a first waterproof outer layer 202 and a first absorbent inner layer 204. The first 13 waterproof outer layer 202 may be made from a semi-rigid material. The first waterproof outer layer 202 may be waterproof such that the face mask 200 is adapted to retain water vapor between the face mask 200 and the face. As a non-limiting example, the face mask 200 may be made of plastic.

The first absorbent inner layer 204 may comprise an absorbent material. The first absorbent inner layer 204 may be saturated with water such that the first absorbent inner layer may release water vapor when heated. 23 A first heating element 206 may heat when an electrical current is passed through the first heating element 206. The first heating element 206 may be disposed throughout the face mask 200 such that heat produced by the first heating element may cause water retained by the first absorbent inner layer 204 to evaporate and form water vapor. As a non-limiting example, the first heating element 206 may be a resistive element embedded within the face mask 200.

The first heating element 206 may be powered from a first power cord 210 via the first thermostat control 212. The first thermostat control 212 may be adapted to control the heat produced within the face mask 200. In some embodiments, the face mask 200 may comprise one or more head straps. The one or more head straps may be adapted to hold the face mask 200 in place on the face.

The chest cover 230 may be a shell that may be adapted to cover the chest of the user 950. The chest cover 230 may be adapted to follow the contours of the chest such that a tight fit is assured. The chest cover 230 may be adapted to cover the front of a torso from a waist to the neck and may extend onto upper arms.

The chest cover 230 may comprise a second waterproof outer layer 232 and a second absorbent inner layer 234. The second waterproof outer layer 232 may be made from a semi-rigid material. The second waterproof outer layer 232 may be waterproof such that the chest cover 230 is adapted to retain water vapor between the chest cover 230 and the chest. As a non-limiting example, the chest cover 230 may be made of plastic.

The second absorbent inner layer 234 may comprise an absorbent material. The second absorbent inner layer 234 may be saturated with water such that the second absorbent inner layer may release water vapor when heated.

A second heating element 236 may heat when an electrical current is passed through the second heating element 236. The second heating element 236 may be disposed throughout the chest cover 230 such that heat produced by the second heating element 236 may cause water retained by the second absorbent inner layer 234 to evaporate and form water vapor. As a non-limiting example, the second heating element 236 may be a resistive element embedded within the chest cover 230.

The second heating element 236 may be powered from a second power cord 240 via the second thermostat control 242. The second thermostat control 242 may be adapted to control the heat produced within the chest cover 230. In some embodiments, the chest cover 230 may comprise one or more torso straps. The one or more torso straps may be adapted to hold the chest cover 230 in place on the chest.

An individual thermostat control selected from the first thermostat control 212 and the second thermostat control 242 may comprise an enclosure 260, an input power cord 262, an output power cord 266, an ON/OFF control 268, and a temperature control 270. The ON/OFF control 268 and the temperature control 270 may be accessible on the exterior of the enclosure 260. The enclosure 260 may shield electrical connections for safety reasons.

The input power cord 262 may be an electrical cord that supplies electrical current to the individual thermostat control from an AC wall plug 264 when the AC wall plug 264 is plugged into a live outlet. The output power cord 266 may supply electrical current from the individual thermostat control to an electrical load. The electrical load may be the first heating element 206 or the second heating element 236.

The ON/OFF control 268 may permit or may block the flow of electrical current through the individual thermostat control. The ON/OFF control 268 may permit the flow of electrical current when the ON/OFF control 268 is in an ON position. The ON/OFF control 268 may block the flow of electrical current when the ON/OFF control 268 is in an OFF position.

The temperature control 270 may determine the amount of electrical current that reaches the load and may thereby control the amount of heat generated within the face mask 200 of the chest cover 230. As non-limiting examples, the temperature control 270 may be a dial or a rocker switch. As non-limiting examples, the dial may be continuously variable from maximum to minimum or may be a multi-position dial with predetermined stops.

The face mask 200 and the chest cover 230 may be adapted to be used simultaneously in order to provide maximum relief. In some embodiments, the face mask 200 may extend downwards such that the bottom of the face mask 200 fits behind the top of the chest cover 230 such that the chest cover 230 assists in holding the face mask 200 in place.

In use, the first absorbent inner layer 204 on the face mask 200 and the second absorbent inner layer 234 on the chest cover 230 may be saturated with water. The face mask 200 may be placed over the face and the chest cover 230 may be placed over the chest. If available, the face mask 200 may be secured using the one or more head straps and the chest cover 230 may be secured using the one or more torso straps. The ON/OFF control 268 on the first thermostat control 212 may be moved to the ON position and the temperature control 270 on the first thermostat control 212 may be set to a desired temperature. The ON/OFF control 268 on the second thermostat control 242 may be moved to the ON position and the temperature control 270 on the second thermostat control 242 may be set to a desired temperature. The face mask 200 and the chest cover 230 may heat the water to form water vapor which may help break up mucus.

Definitions

Unless otherwise stated, the words "up", "down", "top", "bottom", "upper", and "lower" should be interpreted within a gravitational framework. "Down" is the direction that gravity would pull an object. "Up" is the opposite of "down". "Bottom" is the part of an object that is down farther than any other part of the object. "Top" is the part of an object that is up farther than any other part of the object. "Upper" may refer to top and "lower" may refer to the bottom. As a non-limiting example, the upper end of a vertical shaft is the top end of the vertical shaft.

As used in this disclosure, "AC" may be an acronym for alternating current.

As used in this disclosure, an "aperture" may be an opening in a surface or object. Aperture may be synonymous with hole, slit, crack, gap, slot, or opening.

As used herein, the words "control" or "controls" are intended to include any device which can cause the completion or interruption of an electrical circuit; non-limiting examples of controls include toggle switches, rocker switches, push button switches, rotary switches, electromechanical relays, solid state relays, touch sensitive interfaces and combinations thereof whether they are normally open, normally closed, momentary contact, latching contact, single pole, multi-pole, single throw, or multi-throw. In some embodiments, a control may alter an electrical property of a circuit such as resistance, inductance, or capacitance.

As used herein, the word "desired" may refer to a specific value or action within a range of supported values or action. A "desired" value or action may indicate that a range of values or actions is enabled by the invention and that a user of the invention may select a specific value or action within the supported range of values or actions based upon their own personal preference. As a non-limiting example, for a fan that supports operational speed settings of low, medium, or high, a user may select a desired fan speed, meaning that the user may select low, medium, or high speed based upon their needs and preferences at the time of the selection.

As used in this disclosure, the word "exterior" may be used as a relational term that implies that an object is not located or contained within the boundary of a structure or a space.

As used herein, "front" may indicate the side of an object that is closest to a forward direction of travel under normal use of the object or the side or part of an object that normally presents itself to view or that is normally used first. "Rear" or "back" may refer to the side that is opposite the front.

As used in this disclosure, a "heating element" may be a resistive wire that is used to convert electrical energy into heat. As non-limiting examples, common metals used to form heating elements include a combination of nickel and chromium, a combination of iron, chromium and aluminum, a combination of copper, nickel, iron, and manganese, or platinum.

As used herein, "resilient" or "semi-rigid" may refer to an object or material which will deform when a force is applied to it and which will return to its original shape when the deforming force is removed.

As used in this disclosure, a "shell" may be a structure that forms an outer covering intended to contain an object. Shells are often, but not necessarily always, rigid or semi-rigid structures that are intended to protect the object contained within it. Some shells may only partially cover the exterior surface of the object.

As used in this disclosure, a "switch" may be an electrical device that starts and stops the flow of electricity through an electric circuit by completing or interrupting an electric circuit. The act of completing or interrupting the electrical circuit may be called actuation. Completing or interrupting an electric circuit with a switch is often referred to as closing or opening a switch, respectively. Completing or interrupting an electric circuit is also referred to as making or breaking the circuit, respectively.

With respect to the above description, it is to be realized that the optimum dimensional relationship for the various components of the invention described above and in FIGS. 1 through 7, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A heating apparatus for removing mucus comprising:

a face mask and a chest cover;

wherein the face mask is adapted to be worn adjacent to a face and retain water between the face mask and the face;

wherein the chest cover is adapted to be worn adjacent to a chest and retain water between the chest cover and the chest;

wherein the face mask and the chest cover heat when activated and are adapted to evaporate water to create water vapor which breaks up mucus located within the user's sinuses and throat;

wherein the temperatures of the heat created by the face mask and the chest cover are controlled via a first thermostat control and a second thermostat control, respectively;

wherein the face mask comprises a first waterproof outer layer and a first absorbent inner layer;

wherein the first waterproof outer layer is made from a semi-rigid material;

wherein the first waterproof outer layer is waterproof such that the face mask is adapted to retain water vapor between the face mask and the face;

wherein a first heating element heats when an electrical current is passed through the first heating element;

wherein the first heating element is disposed throughout the face mask such that heat produced by the first heating element causes water retained by the first absorbent inner layer to evaporate and form water vapor;

wherein the chest cover comprises a second waterproof outer layer and a second absorbent inner layer;

wherein the second waterproof outer layer is made from a semi-rigid material;

wherein the second waterproof outer layer is waterproof such that the chest cover is adapted to retain water vapor between the chest cover and the chest.

2. The heating apparatus for removing mucus according to claim 1 wherein the face mask is a shell that is adapted to cover the face of a user;

wherein the face mask is adapted to follow the contours of the face;

wherein the face mask is adapted to provide apertures for eyes, mouth, and nostrils;

wherein the face mask is adapted to extends downwards to cover the front of a neck.

3. The heating apparatus for removing mucus according to claim 1 wherein the first absorbent inner layer comprises an absorbent material;

wherein the first absorbent inner layer is saturated with water such that the first absorbent inner layer releases water vapor when heated.

4. The heating apparatus for removing mucus according to claim 3 wherein the first heating element is powered from a first power cord via the first thermostat control;

wherein the first thermostat control is adapted to control the heat produced within the face mask.

5. The heating apparatus for removing mucus according to claim 4 wherein the face mask comprises one or more head straps;

wherein the one or more head straps are adapted to hold the face mask in place on the face.

6. The heating apparatus for removing mucus according to claim 4 wherein the chest cover is a shell that is adapted to cover the chest of the user;

wherein the chest cover is adapted to follow the contours of the chest;

wherein the chest cover is adapted to cover the front of a torso from a waist to the neck and extend onto upper arms.

7. The heating apparatus for removing mucus according to claim 6 wherein the second absorbent inner layer comprises an absorbent material;

wherein the second absorbent inner layer is saturated with water such that the second absorbent inner layer releases water vapor when heated.

8. The heating apparatus for removing mucus according to claim 7 wherein a second heating element heats when an electrical current is passed through the second heating element;

wherein the second heating element is disposed throughout the chest cover such that heat produced by the second heating element causes water retained by the second absorbent inner layer to evaporate and form water vapor.

9. The heating apparatus for removing mucus according to claim 8 wherein the second heating element is powered from a second power cord via the second thermostat control;

wherein the second thermostat control is adapted to control the heat produced within the chest cover.

10. The heating apparatus for removing mucus according to claim 9 wherein the chest cover comprises one or more torso straps;

wherein the one or more torso straps are adapted to hold the chest cover in place on the chest.

11. The heating apparatus for removing mucus according to claim 9 wherein an individual thermostat control selected from the first thermostat control and the second thermostat control comprises an enclosure, an input power cord, an output power cord, an ON/OFF control, and a temperature control;

wherein the ON/OFF control and the temperature control are accessible on the exterior of the enclosure;

wherein the enclosure shields electrical connections for safety reasons.

12. The heating apparatus for removing mucus according to claim 11 wherein the input power cord is an electrical cord that supplies electrical current to the individual thermostat control from an AC wall plug when the AC wall plug is plugged into a live outlet;

wherein the output power cord supplies electrical current from the individual thermostat control to an electrical load;

wherein the electrical load is the first heating element or the second heating element.

13. The heating apparatus for removing mucus according to claim 12 wherein the ON/OFF control permits or blocks the flow of electrical current through the individual thermostat control;

wherein the ON/OFF control permits the flow of electrical current when the ON/OFF control is in an ON position;

wherein the ON/OFF control blocks the flow of electrical current when the ON/OFF control is in an OFF position.

14. The heating apparatus for removing mucus according to claim 13 wherein the temperature control determines the amount of electrical current that reaches the load and thereby controls the amount of heat generated within the face mask of the chest cover.

15. The heating apparatus for removing mucus according to claim 14 wherein the face mask and the chest cover are adapted to be used simultaneously in order to provide maximum relief.

16. The heating apparatus for removing mucus according to claim 15 wherein the face mask extends downwards such that the bottom of the face mask fits behind the top of the chest cover such that the chest cover assists in holding the face mask in place.

* * * * *